(12) United States Patent
Floerke et al.

(10) Patent No.: US 9,862,514 B2
(45) Date of Patent: *Jan. 9, 2018

(54) METHOD AND DEVICE FOR STERILISING EDGES OF PACKAGING MATERIAL

(71) Applicant: SIG Technology AG, Neuhausen am Rheinfall (CH)

(72) Inventors: Rudolf Floerke, Juelich (DE); Hanno Geissler, Krefeld (DE); Hans-Willi Mainz, Heinsberg (DE)

(73) Assignee: SIG Technology AG, Neuhausen am Rheinfall (CH)

(*) Notice: Subject to any disclaimer, the term of this patent is extended or adjusted under 35 U.S.C. 154(b) by 0 days.

This patent is subject to a terminal disclaimer.

(21) Appl. No.: 15/086,849

(22) Filed: Mar. 31, 2016

(65) Prior Publication Data

US 2016/0251100 A1 Sep. 1, 2016

Related U.S. Application Data

(63) Continuation of application No. 14/241,597, filed as application No. PCT/EP2012/063546 on Jul. 11, 2012, now Pat. No. 9,315,284.

(30) Foreign Application Priority Data

Aug. 31, 2011 (DE) .......................... 10 2011 111 523

(51) Int. Cl.
*B65D 25/00* (2006.01)
*A61L 2/18* (2006.01)
(Continued)

(52) U.S. Cl.
CPC ................ *B65B 55/10* (2013.01); *A61L 2/08* (2013.01); *A61L 2/10* (2013.01); *A61L 2/18* (2013.01);
(Continued)

(58) Field of Classification Search
CPC ............................... A61L 2/186; B65B 55/10
See application file for complete search history.

(56) References Cited

U.S. PATENT DOCUMENTS

| 3,187,480 A | 6/1965 | Feeney et al. |
| 3,923,238 A | 12/1975 | Thomas |

(Continued)

FOREIGN PATENT DOCUMENTS

| CN | 2411965 Y | 12/2000 |
| CN | 101460360 A | 6/2009 |

(Continued)

*Primary Examiner* — Kevin Joyner
(74) *Attorney, Agent, or Firm* — The Webb Law Firm

(57) ABSTRACT

Disclosed is a method for processing cut edges of a blank member, so called "package sleeve", made from packaging material, in particular paper/plastics composite material, the cut edges of which are open from above and/or below, by applying a processing medium. In order to develop a simple and cost-effective method, in which the risk of contamination of the packaging and the aseptic region of a filling installation when the package sleeves are filled and closed is reduced, the processing medium contains at least one sterilizing medium and the sterilizing medium remains after being applied to the cut edges and is introduced into the packaging material.

10 Claims, 2 Drawing Sheets

(51) Int. Cl.
*B65B 55/10* (2006.01)
*A61L 2/10* (2006.01)
*A61L 2/22* (2006.01)
*A61L 2/08* (2006.01)
*B65B 55/04* (2006.01)
*B65B 55/08* (2006.01)
*B65D 59/04* (2006.01)

(52) U.S. Cl.
CPC ............. *A61L 2/186* (2013.01); *A61L 2/22* (2013.01); *B65B 55/04* (2013.01); *B65B 55/08* (2013.01); *B65D 25/00* (2013.01); *B65D 59/04* (2013.01)

(56) References Cited

U.S. PATENT DOCUMENTS

| | | | |
|---|---|---|---|
| 4,366,125 A | 12/1982 | Kodera et al. | |
| 4,631,173 A | 12/1986 | Muller et al. | |
| 4,884,694 A * | 12/1989 | Sengewald | A61L 2/26 206/439 |
| 5,122,340 A | 6/1992 | Shimamura et al. | |
| 5,540,885 A | 7/1996 | Pahlmark et al. | |
| 7,776,261 B2 | 8/2010 | Dotsch et al. | |
| 9,034,253 B2 | 5/2015 | Geissler | |
| 2004/0123883 A1 | 7/2004 | Pritchard et al. | |
| 2009/0208369 A1 | 8/2009 | Olsson et al. | |
| 2010/0300044 A1 | 12/2010 | Man et al. | |
| 2012/0076688 A1 * | 3/2012 | Geissler | B65B 3/00 422/28 |

FOREIGN PATENT DOCUMENTS

| | | |
|---|---|---|
| CN | 101607093 A | 12/2009 |
| DE | 2522546 A1 | 12/1975 |
| DE | 3011630 A1 | 10/1981 |
| DE | 3235476 A1 | 5/1983 |
| DE | 68904239 T2 | 5/1993 |
| EP | 0162968 A1 | 12/1985 |
| EP | 0394734 A1 | 10/1990 |
| GB | 1513266 | 6/1978 |
| JP | 958632 A | 3/1997 |
| JP | 2010235206 A | 10/2010 |
| WO | 9618544 A1 | 6/1996 |
| WO | 2008004930 A1 | 1/2008 |
| WO | 2010044024 A1 | 4/2010 |
| WO | 2010142278 A1 | 12/2010 |

* cited by examiner

METHOD AND DEVICE FOR STERILISING EDGES OF PACKAGING MATERIAL

CROSS-REFERENCE TO RELATED APPLICATIONS

This application is a continuation of U.S. patent application Ser. No. 14/241,597 filed Feb. 27, 2014, which claims priority to International Application No. PCT/EP2012/063546 filed Jul. 11, 2012, which claims priority to German Patent Application No. 10 2011 111 523.8 filed Aug. 31, 2011, the disclosures of which are hereby incorporated in their entirety by reference.

BACKGROUND OF THE INVENTION

Field of the Invention

The invention relates to a method for processing cut edges of a blank member ("sleeve") made from packaging material, in particular paper/plastics composite material, the cut edges of which are open from above and/or below, by applying a processing medium and a device for carrying out this method and a packaging sleeve which is processed in accordance with this method.

Description of Related Art

During the production of multi-layer composite packagings, for example, beverage packages, different methods are used.

For example, packages are produced from individual blanks of paper/plastics composite material. In this instance, individual blanks are first obtained from a reel of composite material, and these are subsequently provided with a longitudinal seam. The longitudinal seams are produced by folding and sealing the composite material in such a manner that a product which is intended to fill the package cannot come into contact with an open edge of the composite material.

Such contact could lead to a softening of the packaging material and to a contamination of the product with which it has been filled.

The further processing of packaging sleeves which are produced in this manner, that is to say, the single-sided closing at the upper or lower side of the subsequent package, the sterilisation, the filling and reclosure, is mostly carried out directly in the filling machine.

When the package is produced, the sleeve is first closed at the upper or lower side. Subsequently, the inner side of the package is cleaned and optionally disinfected, before the container which is closed at one side is supplied to the aseptic zone of the filling machine. There, the package is filled and closed. The package is subsequently given its definitive shape. Such a sterilisation method is described, inter alia, in DE 32 35 476 A1.

Regardless of the production method, the closure of the package is generally carried out by pressing and sealing the package material edges, for example, by means of a sonotrode and an anvil. Other methods for closing the packaging are also known, for example, electromagnetic induction or hot air together with mechanical pressing.

The closure of a filled packaging sleeve which is open at one side involves the risk that, in particular when sealing with ultrasound, dust can be thrown out of the packaging material from the open cut edges and it can contaminate both the aseptic region and the open packages.

From the prior art, various methods are known for sealing the edges of packaging blank members of cardboard. The sealing is intended to prevent the penetration of fluid into internal edges of the package after the packaging has been produced.

The generic DE 30 11 630 A1 discloses a method for processing package end faces with an oil which is introduced into the end faces. In this instance, the oil is introduced into all the pores to the greatest possible extent and can be partially polymerised by the effect of heat. The viscosity thereby increases.

WO 96/18544 A1 describes a method for sealing edges of packages with wax, plastics material, adhesive or melt adhesive. The sealing is in this instance applied by means of a nozzle, by means of immersion or spraying. Subsequently, the sealing can be hardened by means of heat.

From U.S. Pat. No. 3,187,480 A, it is known to compress a stack of cardboard blank members and to immerse them in a hot bath of impregnation solution in order to protect the cut edges. Glycine and castor oil are disclosed as an impregnation solution.

SUMMARY OF THE INVENTION

Based on this, an object of the invention is to develop a simple and cost-effective method and a device and a container, in which the risk of contamination of the packages, the product and the aseptic region of a filling installation is reduced when the packages are filled and sealed.

This object is first achieved with a method in which a processing medium contains at least one sterilising medium and a sterilising medium remains after being applied to the cut edges and is introduced into the packaging material.

The cover of packaging material, also referred to as a packaging sleeve, is in particular suitable for producing a package for food products, particularly fluid food products. The packaging material is preferably composite packaging material, in particular paper/plastics material composite packaging material.

Preferably, the packaging sleeves are orientated in an upward direction with the upper and/or lower cut edges during the processing operation using the method according to the invention. The sterilising medium is thus introduced particularly well into the uppermost cardboard layer of the packaging material.

During the exemplary production of paper/plastics composite packaging material, a carrier layer, in most cases paper or cardboard, is coated and in this manner the composite material is produced. Subsequently, the composite material is printed before prefolding and folding lines are applied thereto. In these processing steps, the material is generally a web material. In the next operating step, the packaging material is punched with a "blank" being obtained and layered to form stacks. After this process step, the method according to the invention can be used in an advantageous manner. Subsequently, by folding the blank and connecting the lateral cut edges (longitudinal seam sealing), a package sleeve which is open at the bottom and the top is produced. The method according to the invention is preferably carried out at this location and is therefore not carried out in the aseptic region and even outside the filling machine.

Advantageously, an incubation time is intended to be provided for the sterilising medium. This is in the range from a few minutes to several hours and is sufficient to ensure the disinfection of the edges over the transport time of the package sleeves to the filling machine. Generally, the processing medium remains permanently in the package sleeve.

Optionally, a plurality of package sleeves are packaged in an outer packaging before or after the processing according to the invention. After transport to the filling machine, the package sleeve is folded, shaped and closed at the upper or lower side. After the one-sided closure of the package sleeve, the method according to the invention can also be used. The sterilisation of the inner side of the packaging material is carried out before it is filled and closed in the aseptic region.

The processing is carried out inline or offline with respect to other processing steps. Preferably, the processing medium is fluid and/or is at ambient temperature during the processing operation. The penetration depth of the sterilising medium into the edges of the packaging material is at least 1 mm, preferably between 1 and 2 mm. Depending on the processing medium, the edges may be bleached by this, which is particularly the case when the packaging material comprises or contains unbleached cardboard.

Owing to the additional processing of the open cut edges with sterilising medium and the penetration of the sterilising medium into the packaging material, the open edges and particles which are deposited thereon and/or absorbed thereby, in particular dust, are effectively sterilised and the risk of contamination is thereby reduced.

The application of the sterilising medium to the open cut edges may be carried out by means of a nozzle (spraying), immersion of the cutting edges in a bath, by means of brushes, rollers and/or cylinders.

According to another teaching of the invention, during the application, a plurality of package sleeves are combined in a state folded flat, preferably in an open outer packaging. The objective of this procedure is to use the sterilising medium in the most efficient manner possible.

It is further preferable for the package sleeves to be continuously moved during the processing operation. However, it is also conceivable for the package sleeves not to be moved and for the device to be moved relative to the packaging sleeves in order to apply the processing medium. Various means for continuously moving products or devices are known to the person skilled in the art. In a particularly preferred manner, the package sleeves are moved relative to a nozzle fixed in position by means of a conveyor belt or by means of rollers.

Another teaching of the invention makes provision for the sterilising medium used to be fluid. Preferably, the sterilising medium contains hydrogen peroxide or peracetic acid. In a particularly preferred manner, the hydrogen peroxide content is 35% or the hydrogen peroxide content is only 2% and the sterilising medium is subsequently subjected to UV radiation. It is also advantageous for the processing medium to contain a wetting agent, for example, a surface-active substance, for improved penetration of the processing medium into the packaging material. A preferred mixture relationship is:

Processing medium 1000:Wetting agent 1

In addition or alternatively, the processing medium is an admixture which contains hydrogen peroxide and alcohol and/or in addition an impregnation solution and/or a water-repellent solution. Furthermore, the processing medium may contain an indicator, for example, colour pigments. It is further preferable for the method according to the invention to achieve a reduction of the total colony number determined in accordance with DIN 54379 of at least log 2 (~99%).

According to another teaching of the invention, the processing medium is applied by a nozzle.

According to another embodiment of the invention, it is advantageous if, before the sterilising medium is applied, at least the open cut edges are cleaned in respect of dust, in particular by means of a dust exhaust and/or by means of a stripping device. The stripping device may, for example, be a rotating brush and/or have bristles. If removable dust is already removed before the sterilising medium is applied, this facilitates the penetration of the sterilising medium into the packaging material. Furthermore, dust grains removed before the aseptic region no longer constitute a contamination risk. Furthermore, the contamination of the filling machine, in particular the sealing tools, is thus also reduced and the maintenance and/or cleaning intervals of the sealing tools are extended.

Another preferred embodiment makes provision for the vapours which are produced during the processing operation to be discharged, in particular taken up by an exhaust and supplied to an exhaust air cleaning unit and/or an exhaust air washer. Since the vapours may present a risk to health, the environmental impact can be reduced by a suction operation. In this instance, the relevant provisions are in particular intended to be complied with.

According to another teaching of the invention, the upper and/or lower open cut edges are impregnated. Preferably, the impregnation takes place after the processing with the sterilising medium. Various impregnation means for the impregnation of cut edges are known to the person skilled in the art from the prior art. DE 25 22 546 A1 discloses per se a method for processing the end faces of a roller or a blank with impregnation solution in order to prevent the penetration of fluid into the open edge.

According to another teaching, the package sleeve is irradiated, in particular with UV radiation, beta or gamma radiation. The irradiation is preferably carried out before or after the sterilising medium is applied or after the impregnation. The irradiation alone already has a germicidal effect, but, in the case of irradiation after the sterilising medium has been applied, also further increases the killing effect thereof.

According to another embodiment of the invention, directly after the processing operation, the outer packaging which contains a specific number of package sleeves is closed. This prevents foreign bodies, in particular dust, from becoming deposited on the edges again and not being effectively sterilised and constituting a contamination risk when the package sleeves are closed, after the filling operation in the filling machine. In this instance, it is preferable for the inner sides of the upper and/or lower surfaces of the outer packaging also to be processed with the processing medium. This has the advantage that, after closure, re-contamination of surfaces which have already been processed is reduced. This processing may be carried out, for example, in the same device.

The object is also achieved with a spraying region having at least one nozzle for applying a processing medium which has sterilising medium and a housing which separates at least the spraying region from the environment. The device may have one, two or even more nozzles. Preferably, it additionally has a means for continuously conveying the blanks or packaging sleeves through the at least one spraying region. This may in particular be a conveyor belt, a conveyor roller or another conveying means known to the person skilled in the art.

Upstream and downstream of the device according to the invention, there may be provided devices for carrying out method steps which are before or after the method according to the invention and which are disclosed therewith.

According to another teaching of the invention, the housing comprises an exhaust for drawing off vapours which are produced and/or excess processing medium. In this instance, the exhaust preferably contains a device for cleaning and/or recovery of the sterilising medium.

Another advantageous embodiment of the invention makes provision for a means for dust removal to be provided upstream or downstream of the spraying region. Preferably, the means for dust removal is arranged upstream of the spraying region. A dust exhaust and/or the use of a brush is particularly advantageous for the dust removal.

In order to increase the degree of efficiency of the device, there may be provided a device for impregnation and/or a device for irradiation, in particular with UV, beta or gamma rays. Both devices are preferably arranged downstream of the spraying region. If the device for irradiation is arranged downstream of the device for impregnation, the rays emitted, in addition to their contribution to sterilisation, may also harden the impregnation means.

According to another embodiment of the invention, the nozzle is constructed in such a manner that it can meter and spray at least two materials in a variable manner and/or the spraying angle or the spraying volume can be adjusted. Atomiser nozzles or flat beam nozzles are preferably used. Owing to such an embodiment, the application of the processing medium may be adapted to the size, the shape and the subsequent use of the material to be processed and the required quantity of processing medium may be adjusted.

The object is also achieved with a packaging sleeve where the sterilising medium has been introduced at least into the end region of the upper and/or lower cut edges. Preferably, the sterilising medium is introduced into the packaging material in a range from 1 mm to 2 mm (measured from the cut edge).

A processing of package sleeves in the end region of the upper and/or lower cut edges with sterilising medium sterilises it and particles which are deposited there in an effective manner so that, when the package sleeves are closed after being filled, there is no further risk of germs for the aseptic region and subsequent packaging sleeves from the package sleeves and dust which has accumulated thereon.

In particular when processing unbleached pulp, bleaching may occur at least in the end region of the upper and/or lower cut edges owing to the sterilising medium being introduced, preferably also in the range of a depth of from 1 mm to 2 mm.

The method described above and the device sterilise the open cut edges, and the upper and/or lower inner sides of the outer packaging, in an effective and durable manner so that the edges are still effectively sterilised, even after a period of up to several weeks and after being transported over long distances.

BRIEF DESCRIPTION OF THE DRAWINGS

The invention is explained below with reference to drawings which illustrate merely preferred embodiments.

In the drawings.

DESCRIPTION OF THE INVENTION

Figure 1:
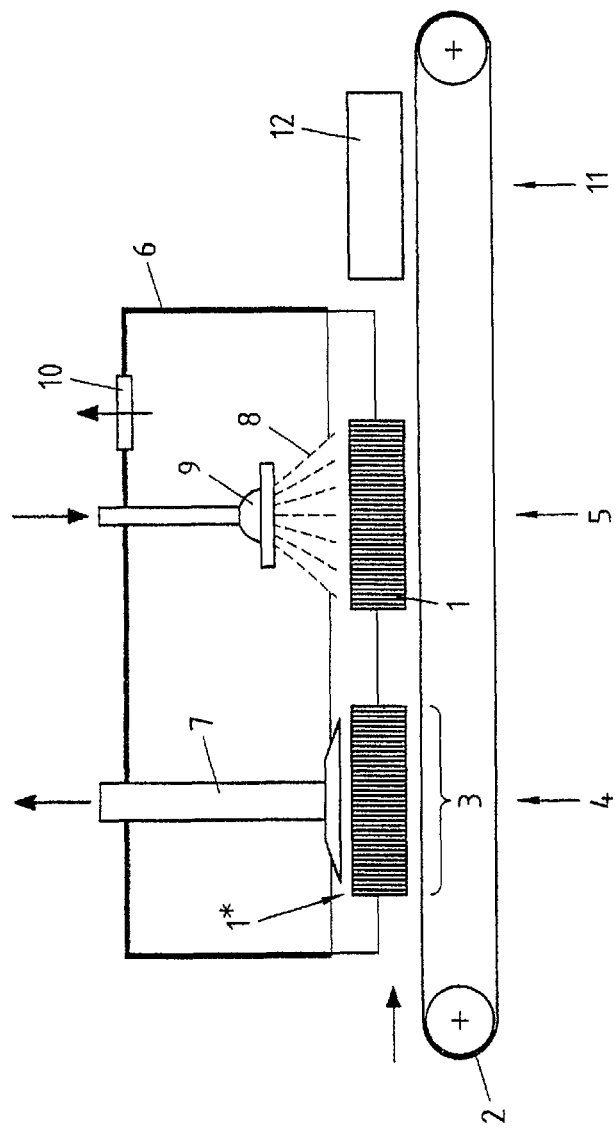
FIG. 1 shows a device for applying a processing medium to open cut edges of a sleeve of packaging material having two processing stations.

FIG. 1 shows an embodiment of a device for processing the upper cut edges 1* of package sleeves 1. The package sleeves 1 are located in a state combined as a group of a plurality of package sleeves 1 in an open outer packaging 3. There is shown a conveyor belt 2 on which the open outer packaging 3 passes through two processing stations 4 and 5. Both processing stations are separated from the environment by a common housing 6.

In the first (optional) processing station 4, particles, in particular dust, are drawn off using a dust exhaust 7 at least from the upper edges of the package sleeves 1. In the next processing station 5, a processing medium 8 which contains a sterilising medium 8 is applied by a nozzle 9 at least to the edges of the package sleeves 1 and can be introduced therein.

The processing medium 8 may additionally contain a wetting medium. Above the processing station 5, an additional exhaust 10 may be provided for drawing off vapours which have occurred during the processing operation. Afterwards, the package sleeves 1 leave the housing 6 in the open outer packaging, after which the outer packaging is closed in a packing station 11. In the closed outer packaging 12, the package sleeves 1 are transported onwards.

Figure 2:
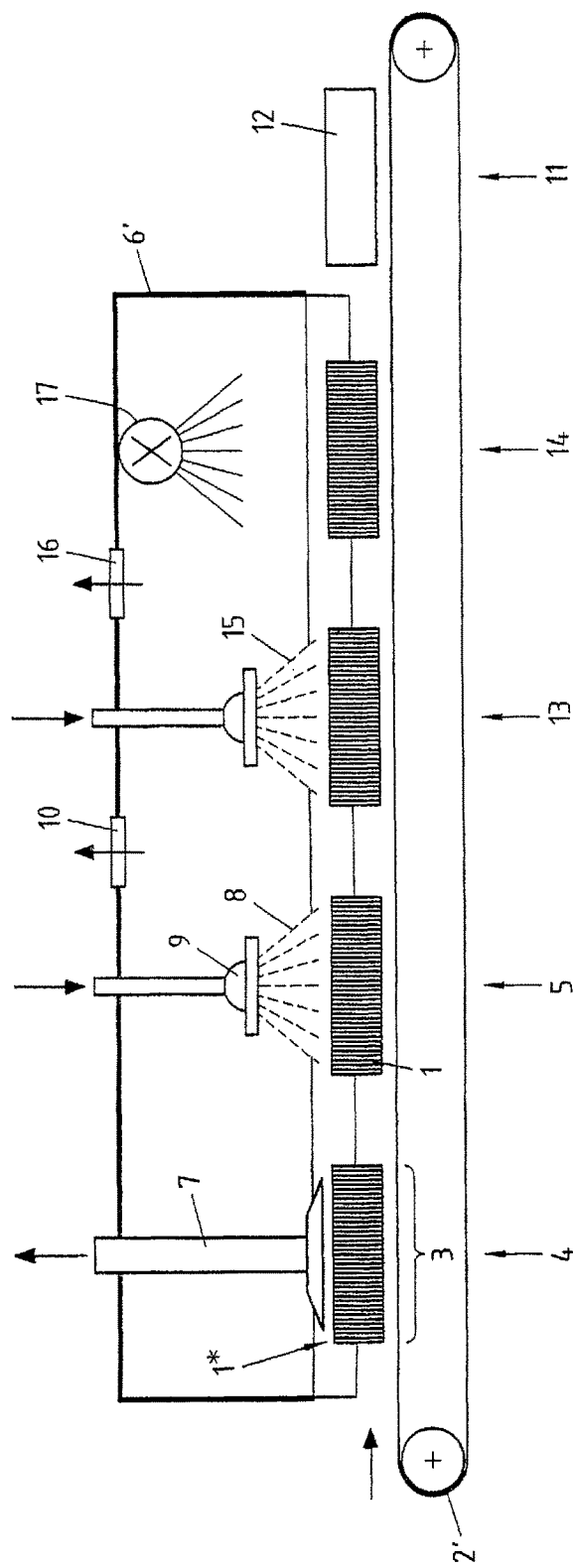
FIG. 2 shows a device for applying a processing medium to open cut edges of a sleeve of packaging material having four processing stations.

FIG. 2 shows another embodiment. The two processing stations 4 and 5 already shown in FIG. 1 are adjoined by a third processing station 13 and a fourth processing station 14, before the open outer packaging 3 is closed in a packing station 11. In this embodiment, all four processing stations 4, 5, 13, and 14 are separated from the environment by means of a conveyor belt 2' through a housing 6'.

The third processing station 13 is optional and impregnates at least the edges 1* of the package sleeves 1 with an impregnation medium 15. Above this processing station 13, there may also be provided an exhaust 16 for drawing off vapours which have occurred during the processing operation. This may be connected to the exhaust 10 of the second processing station 5. The exhausts 10, 16 may be connected to an exhaust air cleaning device (not shown) or an exhaust air washer (not shown).

In the fourth processing station 14, at least the open upper edges of the packaging sleeves 1 are irradiated by a radiation source 17 with UV and/or beta and/or gamma rays. Afterwards, the processed package sleeves 1 leave the housing 6' in the open outer packaging 3, are closed and the closed outer packagings 12 can be transported to the filling location.

Of course, the embodiments shown show only possibilities for configuring the method according to the invention and the corresponding device without constituting a limitation of the devices shown.

The invention claimed is:

1. A package sleeve arrangement for use in making a package, comprising:
    a plurality of adjacent packaging sleeves combined in a folded, flat state, each sleeve made of a packaging material having a first end region containing a first open cut edge, wherein the first end region and the first open cut edge are infiltrated with a sterilising medium.

2. The package sleeve of claim 1 wherein the sleeve comprises a second end region containing a second open cut edge, wherein the second end region and the second open cut edge are infiltrated with a sterilising medium.

3. The package sleeve of claim 1 wherein the sleeve is made of a composite material.

4. The package sleeve of claim 3, wherein the composite material further comprises paper.

5. The package sleeve of claim 4, wherein the composite material further comprises plastic.

6. The package sleeve of claim 1, wherein the sleeve comprises a block having lateral cut edges connected to each other.

7. The package sleeve of claim 6, wherein the lateral cut edges are connected to each other by seam sealing.

8. The package sleeve of claim 1, wherein the sterilising medium includes hydrogen peroxide or peracetic acid.

9. The package sleeve of claim 8, wherein the sterilising medium is fluid.

10. The package sleeve of claim 9, wherein the sterilising medium is at ambient temperature.

* * * * *